United States Patent [19]

Sehmel

[11] 4,159,635

[45] Jul. 3, 1979

[54] ISOKINETIC AIR SAMPLER

[75] Inventor: George A. Sehmel, Richland, Wash.

[73] Assignee: The United States of America as represented by the United States Department of Energy, Washington, D.C.

[21] Appl. No.: 936,461

[22] Filed: Aug. 24, 1978

[51] Int. Cl.² .............................................. G01N 15/00
[52] U.S. Cl. ..................................... 73/28; 73/170 R; 73/421.5 R
[58] Field of Search ................. 73/28, 170 R, 421.5 R

[56] References Cited

U.S. PATENT DOCUMENTS

| | | | |
|---|---|---|---|
| 2,699,679 | 1/1955 | Munger | 73/28 |
| 3,252,323 | 5/1966 | Torgeson | 73/28 |
| 3,261,199 | 7/1966 | Raynor | 73/28 |

Primary Examiner—S. Clement Swisher

Attorney, Agent, or Firm—Dean E. Carlson; Frank H. Jackson

[57] ABSTRACT

An isokinetic air sampler includes a filter, a holder for the filter, an air pump for drawing air through the filter at a fixed, predetermined rate, an inlet assembly for the sampler having an inlet opening therein of a size such that isokinetic air sampling is obtained at a particular wind speed, a closure for the inlet opening and means for simultaneously opening the closure and turning on the air pump when the wind speed is such that isokinetic air sampling is obtained. A system incorporating a plurality of such samplers provided with air pumps set to draw air through the filter at the same fixed, predetermined rate and having different inlet opening sizes for use at different wind speeds is included within the ambit of the present invention as is a method of sampling air to measure airborne concentrations of particulate pollutants as a function of wind speed.

6 Claims, 2 Drawing Figures

ISOKINETIC AIR SAMPLER

CONTRACTUAL ORIGIN OF THE INVENTION

The invention described herein was made in the course of, or under, a contract with the UNITED STATES DEPARTMENT OF ENERGY.

BACKGROUND OF THE INVENTION

This invention relates to an isokinetic air sampler. The invention also relates to a system for taking air samples isokinetically so that the airborne concentration of particulate pollutants can be accurately measured. The invention further relates to a method of sampling air isokinetically to measure airborne concentration of particulate pollutants as a function of wind speed.

Air sampling systems capable of monitoring the atmosphere to determine the extent of pollution by particle emission and to determine how effective antipollution control devices are are well known. Such devices normally use a filter to collect the particles employing an air pump to draw air through the filter. If the air pump is turned on at all times, it is not possible to obtain samples representative of conditions at any particular wind speed; if the air pump is turned on only when the wind speed is at the desired value, air impact pressure will force some air through the filter and cause some particle collection when the air pump is turned off. In addition sampling will not necessarily be isokinetic; i.e., introduced into the sampling system without substantial perturbations of the kinetics of the gas being sampled. If the flow of air around the sampler is at a different speed from the flow of air into the sampler, the sample may not accurately reflect the air being sampled because of the inertia of the particles approaching the sampler.

Monitors have long been known which collect or sample particulate matter from stack gas or any gas flowing through a conduit and isokinetic samplers and techniques for this purpose are well known. The wide variations observed with respect to wind speed, however, do not normally apply to a stack or conduit. Thus samplers and sampling techniques used for air sampling have not heretofore been accurate enough to measure airborne concentrations of particulate pollution as a function of wind speed.

SUMMARY OF THE INVENTION

An isokinetic air sampler includes a filter, a holder for the filter, an air pump for drawing air through the filter at a fixed, predetermined rate, an inlet assembly for the sampler having an inlet opening therein of a size such that isokinetic air sampling is obtained at a particular wind speed, a closure for the inlet opening and means for simultaneously opening the closure and turning on the air pump when the wind speed is such that isokinetic air sampling is obtained. A system incorporating a plurality of such samplers provided with air pumps set to draw air through the filter at the same fixed, predetermined rate and having different inlet opening sizes for use at different wind speeds is included within the ambit of the present invention as is a method of sampling air to measure airborne concentrations of particulate pollutants as a function of wind speed.

BRIEF DESCRIPTION OF THE DRAWINGS

As shown in FIG. 1 an isokinetic air sampler 10 according to the present invention includes a conventional filter 11 carried within a conventional filter holder 12 which includes funnel-shaped outlet 13 terminating in an end fitting 14 to which is attached a high volume air pump 15 (See FIG. 2) for drawing air through the filter. Attached to filter holder 12 is an inlet assembly 16 including a slanting roof 17 which angles up from a flat roof 18 to fit over holder 12. Flat roof 18 is parallel to a bottom member 19, and joined to the bottom member 19 by side walls 21 which together define an inlet opening 20 of predetermined cross sectional area.

Figure 1:
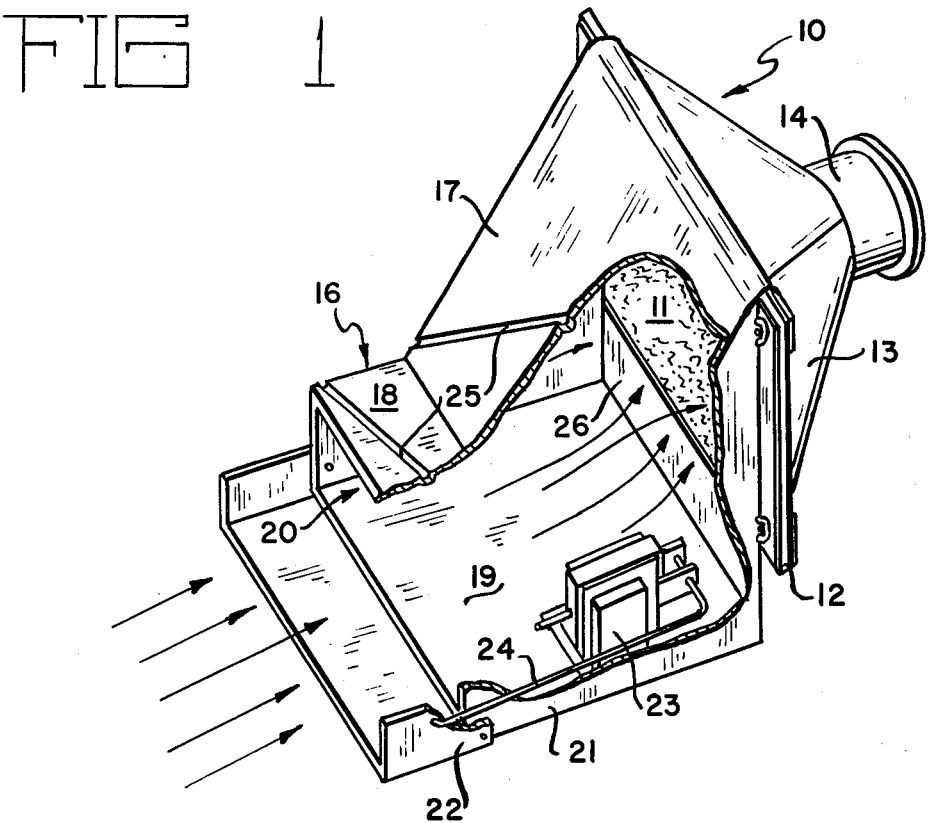
FIG. 1 is a cut-away perspective view of an air sampler constructed in accordance with the present invention.

Inlet opening 20 is provided with a pivotally mounted closure member 22 of greater depth than the inlet opening operated by solenoid 23 through link 24. Both slanting roof 17 and flat roof 18 are provided with rain runoff deflectors 25. In addition an imperforate impact deflector 26 extends upwardly from bottom member 19 to the bottom of the filter—a distance a little greater than the height of inlet opening 20.

Figure 2:
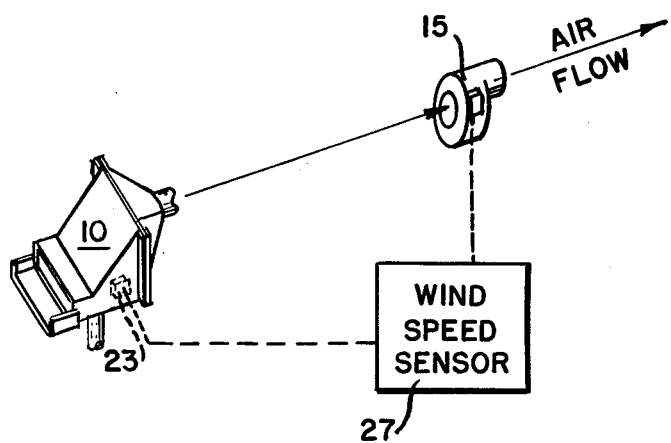
FIG. 2 is a sketch showing an air sampler together with associated equipment.

A plurality of such air samples are employed to provide a system for taking air samples isokinetically at different wind speeds. Each sampler will have a differently sized inlet opening such that for each sampler isokinetic air sampling will be obtained at a different wind speed. Wind speed sensors 27 (See FIG. 2) sense both wind speed and wind direction and open closure member 22 and turn on air pump 15 when the component of wind speed from the direction into which the samplers are facing is at a predetermined value. So that wind gusts will not affect operation, a 15-20 second delay time is built into the system. Thus a set of samplers will cover a complete range of wind speeds within which sampling is to be undertaken and within a set one and only one of the samplers will be operating whenever the wind speed is within the range covered by the set.

The invention will be described in detail as installed at Hanford Works, a Department of Energy installation at Richland, Washington. For a particular investigation a large number of these samplers were mounted at various elevations at various locations all facing in the same direction. The same commercially available filter—a Gelman type A glass fiber filter 20 cm high by 25 cm wide—was employed in each sampler and air was drawn through each filter by an air pump operating at 1.13 cu. meters/min. Also all samplers have a 25 cm. wide inlet opening, the height of the opening being dependent on the wind speed of the air to be sampled. Inlet assembly is formed of 16-gauge aluminum, the flat roof portion of the sampler being 7.5 cm. long and the total distance between inlet opening and filter being 25 cm. The height of the inlet opening is determined as follows:

Flow (cu. meters/min)=windspeed (meters/minute x area of slot) (sq. meters).

Thus the height of the inlet opening to be used at various wind speeds is as follows.

| | | |
|---|---|---|
| 1.5 | meters/sec | 5.0 cm |
| 4 | meters/sec | 1.88 cm |
| 6 | meters/sec | 1.26 cm |
| 9 | meters/sec | 0.84 cm |
| 13 | meters/sec | 0.58 cm |

| | | |
|---|---|---|
| 16 | meters/sec | 0.47 cm |

When an air sampler incorporating an inlet opening of the size given above is employed at or near the appropriate wind speed, isokinetic sampling is attained since the rate of air flow through the opening is approximately that of unimpeded air flow through the same area.

An important feature of the present invention is the separation between respirable and nonrespirable particles attained therein. The total length of the inlet assembly, the length of the inlet portion thereof of unchanging cross section and the impact plate (about 2.5 cm. higher than the height of the inlet opening) are important in attaining this result. It will be noted that the respirable particles rise up to strike the filter rather than the impact plate.

The embodiments of the invention in which an exclusive property of privilege is claimed are defined as follows:

1. An isokinetic air sampler comprising a filter, a holder for the filter, means for drawing air through the filter at a fixed, predetermined rate, an inlet assembly for the sampler having an inlet opening therein of less cross-sectional area than the filter, the size of the opening being such that isokinetic air sampling is obtained at a particular air speed, a closure for the inlet opening and means for simultaneously opening the closure and operating the means for drawing air through the filter when the air speed is such that isokinetic air sampling is obtained.

2. An air sampler according to claim 1 and including an impact plate of greater height than the height of the inlet opening just below the filter, the length of the inlet assembly together with the impact plate resulting in a gross separation between respirable and nonrespirable particles in the samples.

3. An air sampler according to claim 1 wherein the inlet assembly includes a slanting roof portion terminating at the filter and a flat roof portion starting at the inlet opening which holds the cross sectional area of the inlet constant for a limited distance into the sampler.

4. An air sampler according to claim 3 wherein the means for drawing air through the filter operates at a flow rate of 1.13 cu. meters per minute, the filter is 25 centimeters wide and 20 centimeters high and the height of the inlet opening for various air speeds is given in the following table.

| | | |
|---|---|---|
| 1.5 | meters/sec | 5.0 cm |
| 4 | meters/sec | 1.88 cm |
| 6 | meters/sec | 1.26 cm |
| 9 | meters/sec | 0.84 cm |
| 13 | meters/sec | 0.58 cm |
| 16 | meters/sec | 0.47 cm |

5. A system for taking air samples isokinetically at different air speeds comprising a plurality of air samplers constructed as defined in claim 1, said air samplers being provided with air pumps set to draw air through the filter at the same, fixed, predetermined rate and having inlet openings sized to yield isokinetic sampling at different wind speeds.

6. Method for sampling air isokinetically comprising positioning a plurality of air samplers constructed as defined in claim 1 in the atmosphere, said air samplers being constructed to yield isokinetic air sampling at different wind speeds, and turning on only the air sampler with which isokinetic air sampling is most closely approached at the existing wind speed.

* * * * *